United States Patent [19]

Septak

[11] Patent Number: 6,040,182

[45] Date of Patent: Mar. 21, 2000

[54] METHOD AND MATERIALS FOR EFFICIENCY PROTEIN IMMOBILIZATION ON TISSUE CULTURE TREATED ASSAY PLATES

[75] Inventor: Michael Septak, Ashland, Mass.

[73] Assignee: Becton Dickinson and Company, Franklin Lakes, N.J.

[21] Appl. No.: 08/969,081

[22] Filed: Nov. 12, 1997

[51] Int. Cl.[7] ........................................... C12N 5/00
[52] U.S. Cl. ............................ 435/395; 435/29; 435/325; 435/402
[58] Field of Search ............................... 435/395, 29, 325, 435/402

[56] References Cited

U.S. PATENT DOCUMENTS 5,196,309  3/1993  Ginsberg .

*Primary Examiner*—Leon B. Lankford, Jr.
*Attorney, Agent, or Firm*—Bruce S. Weintraub; Nanette S. Thomas

[57] ABSTRACT

The present invention relates to methods and materials for the facilitation of high-protein-binding capability on tissue culture-treated plastic surfaces, such as, for example, polystyrene assay plates.

48 Claims, No Drawings

METHOD AND MATERIALS FOR EFFICIENCY PROTEIN IMMOBILIZATION ON TISSUE CULTURE TREATED ASSAY PLATES

FIELD OF THE INVENTION

The present invention relates to methods and materials for the facilitation of high-protein-binding capability on tissue culture-treated ("TC") plastic assay plates. These methods and materials include the use of appropriate coating buffer ("CB") components to facilitate this high protein-binding capability. Of particular interest within the area of protein immobilization is the immobilization of antibody molecules due to their ease of preparation and high diversity of binding specificity. In particular, the use of organic buffer species which may be capable of acting as surface "charge site modifiers"("CHASM's") and/or "gap-bridges" has been found to enable the use of TC-treated plates as high-protein binding assay plates.

BACKGROUND OF THE INVENTION

Historically, nearly all efforts to achieve efficient protein binding to, for example, polystyrene surfaces by passive, noncovalent adsorption have employed the very basic carbonate or mixed bicarbonate/carbonate buffers at pH 9.6 as CB. See, for example, Butler, J. E. et al., *J. Immunological Methods,* 150: 77–90 (1992). This type of buffer has provided good results when used with classical first-generation hydrophobic assay plates or second-generation hydrophilic assay plates, but not when used with TC-treated plates. If an alternative buffer is employed, it is most commonly phosphate buffer, phosphate-buffered saline or tris buffer at pH of 7.0–8.0. In general, the use of organic CB's other than tris in protein immobilization has been ignored. Certainly, the use of organic CB's in conjunction with TC-treated plates for the purpose of efficient protein immobilization has been ignored, since TC-treated plates have not generally been used to perform heterogeneous immunoassays.

The phenomenon of passive noncovalent binding of protein species to polystyrene is well-known as a practical means of immobilization of assay components, where such immobilization is useful to allow rapid, simple and efficient "bound vs. free" separation(s) to be performed in support of specific detection of particular analyte(s). In general, solid phase binding-based (i.e., heterogeneous) assay formats employ immobilized species ("Capture Antibody" [CAb], if it is an antibody [Ab]) as the starting point for building an appropriate signal-mediating specific binding cascade on the solid support surface. This binding cascade is engineered such that the presence of analyte in the test sample is either: a) required in order to complete the binding cascade, as a necessary prerequisite before signal production may occur ("direct assay" format); or, b) required in order to inhibit binding of a detectable "conjugate" species, which consists of a chemically derivatized version of the analyte (indirect or "inhibition assay" format). The label/reporter species of the conjugate must include functionality which supports detection by appropriate means (e.g., bearing radioisotope, fluorophore or enzyme "label" and/or "reporter" species), while retaining essential binding motifs of the analyte fragment which are required for specific interaction with the CAb species and/or other binding partner(s). With the direct assay format, signal produced in the assay is proportional to the amount of analyte present in the sample. Alternatively in the inhibition assay format, the signal produced by the binding cascade is inversely proportional to the analyte concentration, due to the competition for a limited number of binding cascade sites between analyte (variable amount; detection not facilitated) and conjugate (fixed amount added per tube or well; detectable by design).

In many cases, the protein to be immobilized consists of an antibody (such as, for example, immunoglobulin G [IgG]) which exhibits specific binding with high affinity to the analyte of interest. In other cases, non-antibody proteins which exhibit specific binding capability (e.g., streptavidin, which is known to bind biotin with extremely high specificity and affinity, $K_{eq}$=$10^{15}$ M$^{-1}$) may be immobilized. In general, to be of practical utility, such immobilization needs to exhibit the following properties: a) high efficiency of protein binding (high level of polystyrene surface coverage [about 100–400 ng/cm$^2$], ideally with a high fraction of input protein bound [e.g., 10–99%]); b) high stability of immobilized protein with respect to [undesired] wash-off during "bound vs. free" separation ("wash") steps; c) high retention of native conformation and biological activity; as well as d) high, substantially complete retention of binding properties of the immobilized protein vs. its solution-phase counterpart (in terms of binding affinity, binding specificity and kinetic parameters). Finally, the immobilization process must not introduce conformational or other changes in the CAb or other immobilized species which result in "non-specific binding interactions"(NSB) with other assay reagents and/or sample components. Since in general a large portion of the immobilized CAb (typically about 90% for polyclonal antibodies [pAb's], 90–99% for monoclonal antibodies [mAb's]) or other first binding partner is denatured in the course of immobilization, the latter concern regarding possible NSB is not a trivial one.

The literature, such as Butler et al., supra, indicates that passive adsorption of proteins on polystyrene is an extremely complex, incompletely understood and often unpredictable phenomenon. Historically, assay plate manufacturers have dealt with this serendipitous aspect of the application arena by providing a family of assay plate products which provide a range of polystyrene surface characteristics, from hydrophobic to hydrophilic in character. By screening a variety of tailored surface chemistries for their ability to support efficient immobilization of the desired CAb or other first binding partner, an appropriate solid phase surface chemistry can be selected which allows adequate assay performance to be demonstrated. While it is generally understood that varying the pH of the "Coating Buffer"(CB) used (i.e., the CAb diluent) can modulate the binding obtained, for theoretical reasons primarily related to the presence of a "Linear Binding Region"(LBR) in "% bound" plots of CAb binding as a function of amount of input CAb when using pH 9.6 buffer only as the CB, the vast majority of passive adsorption experiments have employed the carbonate or carbonate/bicarbonate buffer systems at pH 9.6 as "standard CB". The rationale offered for this observation was that the efficiency of passive adsorption is dependent on aggregation of the protein to be immobilized, and that such aggregation was disfavored at pH values more acidic than that of the "standard pH 9.6 CB" when Ab concentration is low. Accordingly, most skilled practitioners of the art employ pH 9.6 buffer(s) (or variants thereof) as CB exclusively, and simply test a large number of possible assay plate types in conjunction with the "standard pH 9.6 CB" to optimize CAb or first binding partner immobilization in their assay development efforts.

It is important to note that early assay plates were either underivatized or lightly derivatized (e.g., gamma irradiated) polystyrene materials of predominately hydrophobic nature.

Later developments in "high protein binding" plates provided considerably more hydrophilic surfaces, e.g. by UV-irradiation of the polystyrene surface. The hydrophilic character of the second-generation assay plates proved to be superior in most cases of protein immobilization, since in general proteins contain a significant density of polar functional groups on their surface. However even using these more polar surfaces, it was evidently still advantageous to work at basic pH to avoid excessive charge density on the protein surface. At pH 9.6, the major difference relative to physiological pH or other more acidic conditions is that free amino groups of the protein are typically partially or completely deprotonated (in free base form, thus neutral with no charge) instead of fully protonated (in positively charged, ammonium ion form).

In parallel to the above developments, a different class of "assay plate" was developed for the purpose of supporting mammalian cell attachment and growth ("tissue culture" [TC] plates). TC plates are prepared using a high energy plasma treatment process under oxidative conditions, either performed under partial vacuum as is done to make Falcon® standard TC and Primaria® TC plates, or alternatively at atmospheric pressure (corona discharge process). These TC plates exhibit a high degree of surface oxidation, and in retrospect it appears that there may be a higher ratio of carboxylate groups present vs. hydroxyl groups, than is the case with classical high protein binding assay plates. Some practitioners do carry out (non-binding based) homogeneous assays in TC plates due to the superior wettability of TC-treated polystyrene plates. Also, some assay developers may indeed have conducted heterogeneous assays with TC-treated plates (e.g., inhibition assays where a high amount of immobilized CAb is not required or desirable). However, the prior literature has not taught knowledgeable practitioners of the art how to effectively employ TC-treated plates as high-protein-binding-capable assay plates on a par in performance with the classical high-protein-binding assay plates. This is accomplished by the methods and materials of the present invention.

SUMMARY OF THE INVENTION

The method of this invention enables the use of TC-treated plastic (such as, for example, polystyrene) assay plates in heterogeneous immunoassay formats by disclosing coating buffers and novel components thereof which overcome the limitations of classical coating methods when used with TC-treated assay plates. In addition, the coating buffers included within the method of this invention are stable at room temperature, unlike, for example, carbonate buffer at pH 9.6. Due to the equilibrium in solution between carbonate ion and gaseous carbon dioxide, the pH of carbonate-based Coating Buffer is a variable which is subject to significant change, e.g. over the course of an overnight coating incubation at room temperature or in shelf storage for a few weeks at room temperature. The lack of such variability should promote more reproducible immobilization, and thus improve overall assay reproducibility (i.e., lower the observed coefficient of variation ["% C.V." ] values).

Furthermore, the novel coating buffer components used in the method of this invention are excellent biological buffers. Combined with the fact that either physiological or near-physiological pH is employed in the method of this invention, this means that it is significantly less likely that CAb or capture protein denaturation should occur during or after immobilization. This aspect of the method of this invention may well be responsible for the surprising differential improvement of the present invention in coating efficiency at low mass input of CAb or capture protein.

The selective ability of added inorganic salt (NaCl) to abolish or greatly reduce protein binding to the TC-treated surface relative to other polystyrene surfaces suggests another role for the organic buffer components of the coating buffers used herein. Because of the presence of ionizable carboxylate groups (i.e., R-COOH $\rightarrow$ R-COO$^-$X$^+$) on TC-treated polystyrene surfaces, and the fact that such groups will be significantly different in character depending on the counterion present, it appears likely that those buffer components which can act as a CHASM species (e.g., bis-tris falls in this category) may promote efficient protein binding in whole or in part by appropriately modifying the inappropriately located R-COO$^{31}$ Na$^+$ sites on the plastic surface such that the alternative R-COO$^-$(bis-tris)-H$^+$ structure, for example, is more compatible with a stable protein binding interaction.

The present invention is thus directed to a method for achieving efficient and stable protein coating on tissue culture-treated plastic surfaces wherein said method comprises:

(a) coating a tissue culture-treated plastic surface with a coating solution wherein the coating solution comprises a protein or polypeptide to be immobilized in a concentration of about 1 ng/mL to about 2000 ng/mL, in a coating buffer, wherein the coating buffer has a buffer species dissolved in distilled and/or deionized water in a concentration of about 2 mM to about 500 mM and in one embodiment the pH of the coating buffer is from about 2 to about 6, in another embodiment the pH of the coating buffer is from about 6 to about 8, and in yet another embodiment, the pH is from about 8 to about 13;

(b) incubating the coating solution on the tissue culture-treated plastic surface;

(c) washing the plastic surface to remove any extraneous materials not firmly attached to the plastic surface;

(d) drying the plastic surface having the coating solution thereon; and (e) obtaining a tissue culture-treated plastic surface having a protein efficiently and stably bound thereto.

DETAILED DESCRIPTION OF THE INVENTION

The method of the present invention is directed to the use of Coating Buffer compositions (CB's), disclosed herein, for the purpose of achieving efficient and stable protein coating on "Tissue Culture-treated"(TC) plastic surfaces (principally, but not limited to, polystyrene, polypropylene, polycarbonate and polyvinyl chloride) by means of a multitude of noncovalent interactions. The key enabling feature of this invention is that the buffer components described herein share the feature that they are capable of interaction with both the protein to be coated and the plastic surface, with the effect that these species act as adapters which improve the fit between binding site and immobilized protein, thus increasing the total amount of protein immobilized, the fraction of immobilized protein which remains biologically active, or both. In addition, these "surface site modifier"(SSM) species serve as the buffering component of the CB in most cases.

The TC-plastic surface is prepared by any one of the usual means, involving exposure of the underivatized plastic surface to a plasma (gaseous mixture of chemically reactive oxygen and/or nitrogen ions and/or free radicals) under controlled conditions at either reduced pressure (true plasma process) or atmospheric pressure (corona discharge process). The TC surface so produced is substantially hydrophilic in character, as compared to the substantially hydrophobic untreated surface.

Other than the use of novel Coating Buffers (CB's) with TC-treated assay plates as disclosed in the method of this invention, protein coating and subsequent use of such coated assay plates in immunoassay applications follows the principles understood by knowledgeable practitioners of the art. These principles have been widely summarized in various books and review articles. Relevant binding interactions include electrostatic (ionic), hydrophobic, hydrogen bonding (H-donor:H-acceptor) and other components. Although no single interaction by itself is strong enough to maintain the bound state, and each interaction may in fact reflect a dynamic equilibrium, if a sufficiently large number of individually weak interactions are established, then the sum total of these interactions supports stable binding since it is statistically unlikely that all of the interactions will be in the "free" state at any given time.

Other than the use of Coating Buffers (CB's) disclosed in the method of this invention, protein coating (passive non-covalent immobilization), rinsing, blocking and drying of assay plates are accomplished by the usual means known to those skilled in the art of heterogenous immunoassay. While a protocol with general utility is described below, it should be understood that a wide variety of procedural and rinse buffer variations may be employed successfully. Optimization of such operations beyond the protocol described below is usually not required, except in rare cases where extreme detection sensitivity and/or reproducibility requirements exist for the assay application.

In a preferred embodiment, the Coating Buffer(s) of the present invention as contemplated are described below as follows.

One or more buffer species of the method of this invention, and, as necessary, other buffers as control(s), are separately dissolved in substantially pure distilled and/or deionized water (free of gross contamination with salts, detergents, organic solvents and especially proteinaceous materials) at low concentration, typically 10 mM (range: 2–500 mM). Filtration to remove undissolved particulates (e.g., using 0.22 μm membrane filter) may then be performed, and is recommended to avoid particle-mediated nonspecific binding (NSB). While typically a single buffer component is used, the use of a mixture of multiple buffer components may in some cases be advantageous, e.g., where $pK_a$ constraints apply relative to the pH to be used. Maintaining good buffering capacity in the CB can be extremely important in ensuring that undesired pH changes do not occur under either storage or coating conditions, as such pH changes can be expected to impact the efficiency and/or reproducibility of coating. A useful rule of thumb is that the working pH (i.e., the final pH of the solution after adjustment using acid or base) of the CB should be within ±1 pH unit of the $pK_a$ of the conjugate acid, to maintain effective buffering capacity. A more conservative rule of thumb is to hold working pH within ±0.7 pH unit of the $pK_a$. In the most favored embodiments of this invention, working pH is established in the range of pH 6–8. In this physiological pH range, the likelihood of protein denaturation under the coating conditions is significantly reduced for most proteins. However, some proteins may be more stable at other (non-physiological) pH values, in which case the use of an alternative working pH would be indicated. Given the tremendous diversity of possible proteins, it is expected that specific cases where the optimum working pH would be in the range of pH 2–6 or pH 8–13 could be found. In such cases, a combination of surface-modifying component(s) below with an appropriate buffering component may be optimal as the Coating Buffer.

Table I below sets forth a variety of buffer components contemplated for utilization in the method of the present invention.

TABLE I

| Trivial Name | (pKa) | typical pH range | Chemical Name |
| --- | --- | --- | --- |
| *bis-tris | 6.5 | 5.8–7.2 | bis(2-hydroxyethyl)-imino-tris-(hydroxymethyl)-methane |
| bis-tris propane | 6.8 | 6.1–7.5 | 1,3-bis-(tris-[hydroxymethyl]methylamino)-propane |
| " | 9.0 | 8.3–9.7 | " |
| citrate | 3.1 | 2.4–3.8 | citric acid |
| " | 4.8 | 4.1–5.5 | " |
| " | 6.4 | 5.7–7.1 | " |
| *HEPES | 7.5 | 6.8–8.2 | N-(2-hydroxyethyl)-piperazine-N-(2-ethanesulfonic acid) |
| glycinamide | 8.1 | 7.4–8.8 | aminoacetamide |
| glycine | 2.4 | 1.7–3.1 | aminoacetic acid |
| " | 9.8 | 9.1–10.5 | " |
| glycl-glycine | 3.1 | 7.5–8.9 | N-(glycl)-glycine |
| " | 8.2 | 7.5–8.9 | " |
| *histidine | 6.0 | 5.3–6.7 | 2-amino-3-imidazolylpropionic acid |
| *imidazole | 7.0 | 6.3–7.7 | imidazole |
| *MES | 6.1 | 5.4–6.8 | 2-(N-morpholino)-ethanesulfonic acid |
| *MOPS | 7.2 | 6.5–7.9 | 3-(N-morpholino)-propanesulfonic acid |
| tris | 8.1 | 7.4–8.8 | tris-(hydroxymethyl)-aminomethane |

*Particularly favored "surface site modifier" (SSM) species.

Additional favored SSM species include the so-called "Good" buffers which are not already listed above; see W. J. Ferguson and N. E. Good, *Anal. Biochem* 104: 300 (1980), and references therein. These include ADA, ACES, PIPES, MOPSO, BES, TES, DIPSO, TAPSO, HEPPSO, POPSO, EPPS, TEA, tricine, bicine, TAPS, AMPSO, CHES, CAPSO, AMP and CAPS.

The coating solution(s) can be prepared as follows. The protein or polypeptide to be immobilized (as first binding partner in a binding cascade appropriate for the end assay application) is dissolved in the CB(s) prepared as described above, at a concentration (typically, 1–2000 ng/mL) appropriate to the assay application. The Coating Solution(s) so prepared (CS[s]) are typically used immediately, although short-term storage in suitable non-protein adsorbing vessel (s) may be allowed for convenience. However, the risk of undesired adsorption under even short-term storage conditions is always a possibility.

In a preferred embodiment, the method for coating the TC-plate is set forth below as follows.

1) Plate Coating

While no pretreatment of the plates is necessarily required, some users prefer to rinse the wells (typically, 1–3 iterations) with a protein-free, detergent-free buffer solution (e.g., the corresponding CB from which the CS was prepared), and/or distilled and/or deionized water, prior to addition of CS. With appropriate CS(s) in hand, coating is commenced by simply pipetting the CS(s) separately into wells on the assay plate(s) to be coated. Passive adsorption of protein to the plate surface is allowed to proceed for an appropriate time interval, which must be determined experimentally and is a function of the protein used, the assay application, and many other factors. One such additional factor is the temperature of incubation, which is typically in the range of 4–37° C. inclusive, although more extreme temperatures could conceivably be suitable or advantageous (e.g., use of higher temperature than 37° C. with a protein which is known to be unusually thermostable).

2) Post-Coating Rinses

Rinsing of wells (typically, 1–3 iterations) prior to blocking may or may not be required. If post-coating rinses are to be done, protein-free, detergent-free buffer solutions should in general be used. Such Rinsing Buffer (RB) could be, for example, phosphate-buffered saline (PBS), or a wide variety of other possibilities which are evident to those practiced in the art of passive protein adsorption. Even (unbuffered) water may be used in some cases. It is important to understand that such rinses may introduce potential artifacts into the system, if inappropriate components such as exogenous protein(s), detergents, organic solvents, and/or other chemicals such as enzyme inhibitors are present. For example, rinses performed with detergent present in the RB will usually prevent subsequent blocking from being efficient, however, such an approach may be acceptable since the detergent itself may have blocking capability (e.g., polyoxyethylene-based detergent Tween-20).

3) Blocking

Blocking with a concentrated solution (typically, 0.01–100 mg/mL) of an economical, readily available protein or proteinaceous mixture such as bovine serum albumin (BSA), nonfat dry milk (NFDM) or many other commercially available reagents and/or mixtures is performed in a manner completely consistent with the prior art. However, such protein-based blocking may or may not be required to achieve low NSB in the assay application. Alternatively, as alluded to above regarding the detergent Tween-20, in some cases acceptable blocking performance is achievable using non-proteinaceous blocker species. With or without such protein-based blocking, the next step is usually to proceed to washing.

4) Post-Blocking Washes

Coated, blocked wells can be washed serially (typically, 1–3 iterations) with an appropriate Wash Buffer (WB) in a manner completely consistent with the prior art. As with RB above, a wide variety of compositions may be effective. Typically, a detergent such as Tween-20 is included at a concentration below its critical micellar concentration (CMC). Use of detergent in this step is usually desirable to remove excess blocking agent and/or coating protein of interest, but is not necessarily required.

5) Drying

Plates are dried in a manner completely consistent with the prior art. For example, overnight drying in a vacuum oven (at ambient temperature to 37° C.) is typically effective. In order to maintain dryness, subsequent storage under desiccated conditions in the absence of light is preferred. However, if storage is not required, plates are usable in the assay application immediately upon completion of steps 1 through 4 above.

The following Examples are intended to be demonstrative and are not intended to limit the present invention in any way.

EXAMPLE I

It was found that, for TC-treated plates only, the use of phosphate buffer at pH 7.2 (both Dulbecco's PBS and especially, 10 mM phosphate with no added salt) provided significantly higher protein binding results than those obtained using the "standard pH 9.6 CB" as purchased commercially (with storage of 10=stock at 4° C.) or prepared fresh the same day. Effects of significant magnitude (about 2-fold to 3-fold) were observed at high capture antibody ("CAb" input (e.g., 1000 ng/well). However, differences were especially striking at low CAb input (20-fold to 100-fold higher at 30 ng/well input CAb). Moreover, TC-treated plates loaded with CAb using the physiological pH CB approach provided comparable signal levels to those observed in parallel assays using a panel of high-protein-binding plates (Nunc Maxisorp, Corning High-Binding & Dynex Immulon-4; regardless of CB used), with lower non-specific binding (NSB) background. These differences appeared particularly notable, in view of the literature claim that for the high protein binding plates known heretofore in the art, that only use of the pH 9.6 type of buffer could support efficient protein binding at low CAb mass input levels. (Butler, et al., supra) It was also evident that efficient CAb binding to TC-treated plates was much more disrupted by the presence of added salt (NaCl) in the CB than was the case with classical high-protein-binding plates (B. D. Labware N. B. #110, pp.52–56).

With the above results in hand, it was of interest to systematically investigate the buffer dependence of CAb immobilization by adsorption on TC-treated plates. CAb immobilization was studied at both high (1000 ng/well) and low (20 ng/well) mass input of CAb. In experiments using two different model CAb species, rabbit anti-(goat IgG) and mouse anti-(goat IgG) polyclonal antibodies ("pAb's"), it was apparent that a number of different 10 mM organic buffers at pH 5.0–7.2 provided results superior to those with either the "standard pH 9.6 CB" or even 10 mM phosphate at pH 7.2. The best of these buffers was "bis-tris" at pH 6.0, i.e. bis-(2-hydroxyethyl)-imino-tris-(hydroxymethyl)-methane. Other buffers which exhibited significant improvement vs. phosphate at pH 7.2 were MES [2-(N-morpholino)-ethanesulfonic acid], citrate and histidine at pH 6.0, as well as HEPES [N-(2-hydroxyethyl) piperazine-N'-(2-ethanesulfonic acid)], imidazole and MOPS [3-(N-morpholino) propanesulfonic acid] at pH 7.2. All organic buffers tested provided better results than the "standard pH 9.6 CB", although "bis-tris propane" at pH 9.7 was much less effective than bis-tris propane at pH 7.2 (which was comparable in results to phosphate at pH 7.2), indicating that the use of organic buffer at the very basic classical coating pH of 9.6 is in general inferior to working at or near physiological pH (i.e., pH 6.0–8.0) (B. D. Labware N. B. #110, pp. 65–77). In contrast to the above results with TC-treated plates, with representative classical assay plates (for example, Falcon #3915 Pro-Bind), relatively little variation in protein binding efficiency as a function of the CB used was observed. However, even with the classical plates, use of organic CB in the method of this invention may in some cases provide moderately superior protein coating efficiency than that with classical pH 9.6 CB formulations.

Experiments on the immobilization of streptavidin as a model non-antibody capture protein demonstrated similar results to the above Ab immobilization work on TC-treated Falcon plates (again, best results were seen with bis-tris at pH 6.0) (B.D. Labware N.B. #110 pp. 81–87).

EXAMPLE II

In order to demonstrate the advantages of the method of this invention in an aggressively stressed assay context, a study was done using a model assay format in which a sandwich assay to detect goat pAb mock analyte under conditions of high "spike dilution" of the analyte was conducted. The assay format consisted of a) rabbit anti-(goat IgG) pAb ("RAG") as the immobilized CAb; b) mixed analyte consisting of biotinylated goat anti-(human IgG) pAb ("bio-GAH") plus unlabeled goat anti-(human IgG) pAb ("GAH") at 1:2000 molar ratio (i.e., 1:2000 bio-GAH:GAH spike dilution); and finally, c) streptavidin horseradish peroxidase ("SA-HRP") conjugate. In order to obtain signal in the enzyme-linked immunosorbent assay (ELISA), the CAb must pull out the mixture of bio-GAH and GAH, whereas only bio-GAH will be able to bind SA-HRP conjugate and thus be subsequently detected. In this fashion, high binding capability can be demonstrated under conditions where signal development in the assay is relatively slow and controllable, and meaningful comparative results can be obtained with a reasonably long substrate incubation time which is reproducible from plate to plate. Another advantage of this approach is that it is easy to stay within the linear range of signal generation, to ensure that absorbance data obtained are reflective of the relative levels of bound conjugate in the wells. If signal generation is allowed to proceed too long, i.e. into the nonlinear range, then product inhibition may act as a spurious leveling factor to compress the range of results.

Using the above assay format, a dilution series of RAG CAb was prepared and immobilized, in the range of 1000 ng/well to 10 ng/well, concurrently on Falcon TC (#3075), Corning Cell Wells TC, Falcon Pro-Bind (#3915) and Nunc Maxisorp plates. In the assay, a constant input level of total analyte of 1000 ng/well of 1:2000 bio-GAH:GAH was added. The results (see notebook copy of Excel spreadsheet "623-RAG-hi-bind-optimizing") confirmed that the TC-treated plates exhibited negligible assay signal levels using the "standard pH 9.6 carbonate CB"(with Corning TC) or phosphate buffer at pH 7.2 (Falcon TC). On the other hand, using bis-tris at pH 6.0 as CB, both TC-treated plates exhibited results either comparable to Nunc Maxisorp (Corning TC) or nearly so (Falcon TC) (B. D. Labware N. B.#110, pp. 101–109).

What is claimed is:

1. A method for achieving efficient and stable protein coating on plasma treated plastic surfaces wherein said method comprises:

(a) coating a plasma treated plastic surface with a coating solution wherein said coating solution comprises a protein or polypeptide to be immobilized in a concentration of about 1 ng/mL to about 2000 ng/mL, in a coating buffer, wherein said coating buffer has a buffer species dissolved in distilled or deionized water in a concentration of about 2 mM to about 500 mM and the pH of the coating buffer is from about 6 to about 8;

(b) incubating said coating solution on said plasma treated plastic surface;

(c) washing the plastic surface to remove any extraneous materials not firmly attached to the plastic surface;

(d) drying the plastic surface having the coating solution thereon; and (e) obtaining a plasma treated plastic surface having a protein efficiently and stably bound thereto.

2. The method of claim 1 wherein prior to step (a), the plastic surface is washed with a buffer solution.

3. The method of claim 2 wherein said buffer solution is a coating buffer having a buffer species dissolved in distilled or deionized water in a concentration of about 2 mM to about 500 mM.

4. The method of claim 1 wherein said plastic surface is selected from the group consisting of polystyrene, polypropylene, polycarbonate and polyvinyl chloride.

5. The method of claim 1 wherein the incubation of step (b) occurs at a temperature of about 4° C. to about 37° C.

6. The method of claim 1 wherein the incubation of step (b) occurs at a temperature of about 37° C. or higher.

7. The method of claim 1 wherein after step (b) the plastic surface is rinsed with a buffer solution.

8. The method of claim 7 wherein said buffer solution is a protein-free, detergent-free solution.

9. The method of claim 8 wherein said buffer solution is water or phosphate-buffered saline.

10. The method of claim 1 wherein, after step (b), a blocking agent is applied to said plasma treated plastic surface wherein said blocking agent has a concentration of from about 0.01 to about 100 mg/mL of a second protein, proteinaceous mixture or non-proteinaceous blocking agent; and in step (d) the plastic surface is also washed to remove any excess blocking agent which is still on the plastic surface.

11. The method of claim 7 wherein, after rinsing the plastic surface with a buffer solution, a blocking agent is applied to the plasma treated plastic surface wherein said blocking agent has a concentration of from about 0.01 to about 100 mg/mL of a second protein proteinaceous mixture or non-proteinaceous blocking agent; and in step (d) the plastic surface is also washed to remove any excess blocking agent which is still on the plastic surface.

12. The method of claim 10 wherein a detergent is included in washing the plastic surface to remove excess blocking agent.

13. The method of claim 11 wherein a detergent is included in washing the plastic surface to remove excess blocking agent.

14. The method of claim 2 wherein after step (b), the plastic surface is rinsed with a buffer solution.

15. The method of claim 14 wherein, after rinsing the plastic surface with a buffer solution, a blocking agent is applied to the tissue culture-treated plastic surface wherein said blocking agent has a concentration of from about 0.01 to about 100 mg/mL of a second protein, proteinaceous mixture and/or non-proteinaceous blocking agent; and in step (d) the plastic surface is also washed to remove any excess blocking agent which is still on the plastic surface.

16. The method of claim 15 wherein in step (d) a detergent is included in washing the plastic surface to remove excess blocking agent.

17. A method for achieving efficient and stable protein coating on plasma treated plastic surfaces wherein said method comprises:

(a) coating a plasma treated plastic surface with a coating solution wherein said coating solution comprises a protein or polypeptide to be immobilized in a concentration of about 1 ng/mL to about 2000 ng/mL, in a coating buffer, wherein said coating buffer has a buffer species dissolved in distilled or deionized water in a concentration of about 2 mM to about 500 mM and the pH of the coating buffer is from about 2 to about 6;

(b) incubating said coating solution on said plasma treated plastic surface;

(c) washing the plastic surface to remove any extraneous materials not firmly attached to the plastic surface;

(d) drying the plastic surface having the coating solution thereon; and (e) obtaining a plasma treated plastic surface having a protein efficiently and stably bound thereto.

18. The method of claim 17 wherein prior to step (a), the plastic surface is washed with a buffer solution.

19. The method of Claim 18 where in said buffer solution has a buffer species dissolved in distilled or deionized water in concentration of about 2 mM to about 500 mM.

20. The method of claim 17 wherein said plastic surface is selected from the group consisting of polystyrene, polypropylene, polycarbonate and polyvinyl chloride.

21. The method of claim 17 wherein the incubation of step (b) occurs at a temperature of about 4° C. to about 37° C.

22. The method of claim 17 wherein the incubation of step (b) occurs at a temperature of about 37° C. or higher.

23. The method of claim 17 wherein after step (b) the plastic surface is rinsed with a buffer solution.

24. The method of claim 23 wherein said buffer solution is a protein-free, detergent-free solution.

25. The method of claim 24 wherein said buffer solution is water or phosphate-buffered saline.

26. The method of claim 17 wherein, after step (b), a blocking agent is applied to the plasma treated plastic surface wherein said blocking agent has a concentration of from about 0.01 to about 100 mg/mL of a second protein, proteinaceous mixture and/or non-proteinaceous blocking agent; and in step (d) the plastic surface is also washed to remove any excess blocking agent which is still on the plastic surface.

27. The method of claim 23 wherein, after rinsing the plastic surface with a buffer solution, a blocking agent is applied to the plasma treated plastic surface wherein said blocking agent has a concentration of from about 0.01 to about 100 mg/mL of a second protein, proteinaceous mixture and/or non-proteinaceous blocking agent; and in step (d) the plastic surface is also washed to remove any excess blocking agent which is still on the plastic surface.

28. The method of claim 26 wherein in step (d) a detergent is included in washing the plastic surface to remove excess blocking agent.

29. The method of claim 27 wherein a detergent is included in washing the plastic surface to remove excess blocking agent.

30. The method of claim 18 wherein after step (b), the plastic surface is rinsed with a buffer solution.

31. The method of claim 30 wherein, after rinsing the plastic surface with a buffer solution, a blocking agent is applied to the plasma treated plastic surface wherein said blocking agent has a concentration of from about 0.01 to about 100 mg/mL of a second protein, proteinaceous mixture and/or non-proteinaceous blocking agent; and in step (d) the plastic surface is also washed to remove any excess blocking agent which is still on the plastic surface.

32. The method of claim 31 wherein a detergent is included in washing the plastic surface to remove excess blocking agent.

33. A method for achieving efficient and stable protein coating on plasma treated plastic surfaces wherein said method comprises:

(a) coating a plasma treated plastic surface with a coating solution wherein said coating solution comprises a protein or polypeptide to be immobilized in a concentration of about 1 ng/mL to about 2000 ng/mL, in a coating buffer, wherein said coating buffer has a buffer species dissolved in distilled or deionized water in a concentration of about 2 mM to about 500 mM and the pH of the coating buffer is from about 8 to about 13;

(b) incubating said coating solution on said plasma treated plastic surface;

(c) washing the plastic surface to remove any extraneous materials not firmly attached to the plastic surface;

(d) drying the plastic surface having the coating solution thereon; and (e) obtaining a plasma treated plastic surface having a protein efficiently and stably bound thereto.

34. The method of claim 33 wherein prior to step (a), the plastic surface is washed with a buffer solution.

35. The method of claim 34 wherein said buffer solution has a buffer species dissolved in distilled or deionized water in a concentration of about 2 mM to about 500 mM.

36. The method of claim 33 wherein said plastic surface is selected from the group consisting of polystyrene, polypropylene, polycarbonate and polyvinyl chloride.

37. The method of claim 33 wherein the incubation of step (b) occurs at a temperature of about 4° C. to about 37° C.

38. The method of claim 33 wherein the incubation of step (b) occurs at a temperature of about 37° C. or higher.

39. The method of claim 33 wherein after step (b) the plastic surface is rinsed with a buffer solution.

40. The method of claim 39 wherein said buffer solution is a protein-free, detergent-free solution.

41. The method of claim 40 wherein said buffer solution is water or phosphate-buffered saline.

42. The method of claim 33 wherein, after step (b), a blocking agent is applied to the said plasma treated plastic surface wherein said blocking agent has a concentration of from about 0.01 to about 100 mg/mL of a second protein, proteinaceous mixture or non-proteinaceous blocking agent; and in step (d) the plastic surface is also washed to remove any excess blocking agent which is still on the plastic surface.

43. The method of claim 39 wherein, after rinsing the plastic surface with a buffer solution, a blocking agent is applied to the tissue culture-treated plastic surface wherein said blocking agent has a concentration of from about 0.01 to about 100 mg/mL of a second protein, proteinaceous mixture and/or non-proteinaceous blocking agent; and in step (d) the plastic surface is also washed to remove any excess blocking agent which is still on the plastic surface.

44. The method of claim 42 wherein in step (d) a detergent is included in washing the plastic surface to remove excess blocking agent.

45. The method of claim 43 wherein a detergent is included in washing the plastic surface to remove excess blocking agent.

46. The method of claim 34 wherein after step (b), the plastic surface is rinsed with a buffer solution.

47. The method of claim 46 wherein, after rinsing the plastic surface with a buffer solution, a blocking agent is applied to the tissue culture-treated plastic surface wherein said blocking agent has a concentration of from about 0.01 to about 100 mg/mL of a second protein, proteinaceous mixture and/or non-proteinaceous blocking agent; and in step (d) the plastic surface is also washed to remove any excess blocking agent which is still on the plastic surface.

48. The method of claim 47 wherein a detergent is included in washing the plastic surface to remove excess blocking agent.

\* \* \* \* \*